(12) United States Patent
Fima

(10) Patent No.: US 11,401,492 B2
(45) Date of Patent: *Aug. 2, 2022

(54) METHODS AND SYSTEMS FOR IN-VITRO MILK PRODUCTION

(71) Applicant: Biomilk Ltd., Rehovot (IL)

(72) Inventor: Sharon Fima, Kfar-HaNagid (IL)

(73) Assignee: Biomilk Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/542,568

(22) Filed: Dec. 6, 2021

(65) Prior Publication Data

US 2022/0089993 A1    Mar. 24, 2022

Related U.S. Application Data

(63) Continuation of application No. 17/383,495, filed on Jul. 23, 2021, now Pat. No. 11,236,299.

(60) Provisional application No. 63/075,476, filed on Sep. 8, 2020.

(51) Int. Cl.
| | |
|---|---|
| *C12N 5/071* | (2010.01) |
| *C12M 1/12* | (2006.01) |
| *C12P 21/00* | (2006.01) |
| *C12M 1/00* | (2006.01) |
| *C07K 14/47* | (2006.01) |
| *C12M 1/32* | (2006.01) |
| *A23C 9/152* | (2006.01) |
| *A23C 9/12* | (2006.01) |

(52) U.S. Cl.
CPC ............ *C12M 25/10* (2013.01); *A23C 9/152* (2013.01); *C07K 14/47* (2013.01); *C07K 14/4732* (2013.01); *C12M 23/12* (2013.01); *C12M 41/14* (2013.01); *C12N 5/0631* (2013.01); *C12P 21/00* (2013.01); *C12N 2533/50* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 11,111,477 B2* | 9/2021 | Strickland | ............ C12N 5/0631 |
| 11,236,266 B2 | 2/2022 | Sun et al. | |
| 2011/0236299 A1 | 9/2011 | Gao et al. | |
| 2015/0079584 A1 | 3/2015 | Gevaert et al. | |
| 2017/0267970 A1* | 9/2017 | Gupta | .................. C12N 5/0068 |

(Continued)

FOREIGN PATENT DOCUMENTS

| | | |
|---|---|---|
| CN | 110272824 | 9/2019 |
| WO | WO 2021/014221 | 1/2021 |

(Continued)

OTHER PUBLICATIONS

Cho, Youngkyu; et al; "Construction of a 3D mammary duct based on spatial localization of the extracellular matrix" NPG Asia Materials, 10, 970-981, 2018 (Year: 2018).*

(Continued)

*Primary Examiner* — David W Berke-Schlessel

(57) ABSTRACT

The disclosure relates to methods, systems and compositions for use in the production of milk. More specifically, the disclosure is directed to systems, compositions and methods for in-vitro production of milk using an array of mammary organoids seeded on tertiary-branched, resilient duct scaffolding.

17 Claims, 1 Drawing Sheet

(56) References Cited

U.S. PATENT DOCUMENTS

Figure 1:
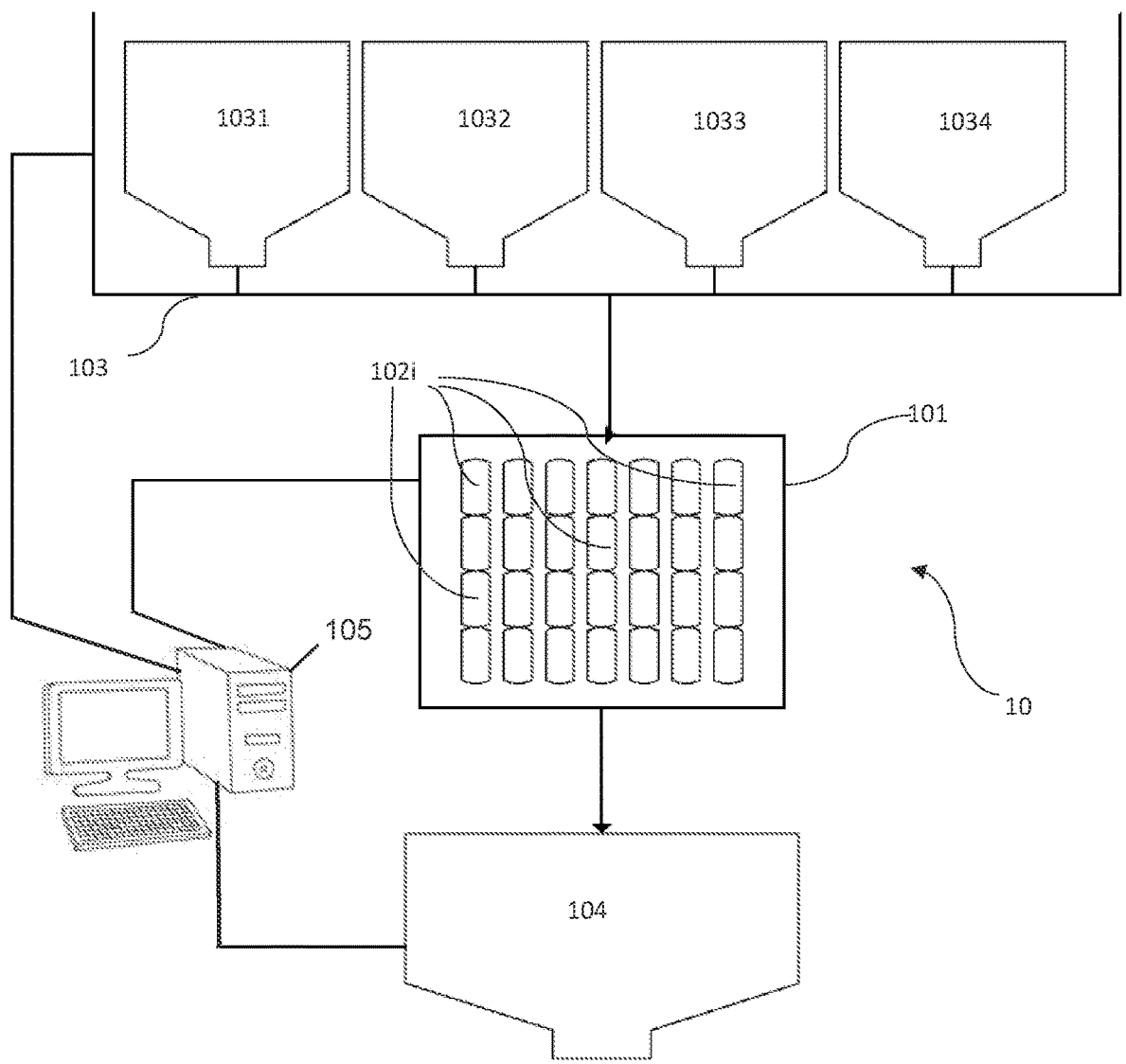

2018/0066220 A1* 3/2018 Nath .............. C12M 21/08
2019/0211296 A1 7/2019 Allbritton
2021/0207090 A1 1/2021 Strickland

FOREIGN PATENT DOCUMENTS

WO  WO 2021/141762  7/2021
WO  WO 2021/142241  7/2021

OTHER PUBLICATIONS

Official Action dated Feb. 4, 2022 From the Re. U.S. Appl. No. 17/542,551. (6 Pages).
International Search Report and the Written Opinion dated Nov. 17, 2021 From the International Searching Authority Re. Application No. PCT/IL2021/051094 (10 Pages).
Notice of Allowance dated Nov. 16, 2021 from Re. U.S. Appl. No. 17/383,495. (10 pages).
Cho et al. "Construction of a 3D Mammary Duct Based on a Spatial Localization of the Extraxcellular Matrix", NPG Asia Materials, 10: 970-981, 2018.
Official Action dated Mar. 4, 2022 from Re. U.S. Appl. No. 17/542,570. (14 pages).
Official Action dated Mar. 4, 2022 from Re. U.S. Appl. No. 17/542,599. (14 pages).
Final Official Action dated Mar. 9, 2022 from Re. U.S. Appl. No. 17/542,551. (11 pages).
Official Action dated Feb. 17, 2022 from Re. U.S. Appl. No. 17/1542,552. (12 pages).

* cited by examiner

METHODS AND SYSTEMS FOR IN-VITRO MILK PRODUCTION

RELATED APPLICATIONS

This application is a continuation of U.S. patent application Ser. No. 17/383,495 filed on Jul. 23, 2021, which claims the benefit of priority under 35 USC § 119(e) of U.S. Provisional Patent Application No. 63/075,476 filed on Sep. 8, 2020. The contents of the above applications are all incorporated by reference as if fully set forth herein in their entirety.

FIELD AND BACKGROUND OF THE INVENTION

The disclosure is directed to methods, systems and compositions for use in the production of milk More specifically, the disclosure is directed to systems, compositions and methods for in-vitro production of milk using an array of mammary organoids seeded on tertiary-branched, resilient duct scaffolding.

The global dairy market, comprising the processing and harvesting of animal milk for human consumption, reached a value of US$ 718.9 Billion in 2019, and is typically sourced from cow, goat, buffalo, camel and sheep. With widespread demand for dairy products and their proactive function in the global food industry, dairy plays a crucial role in the growth of the economies worldwide.

Existing dairy milk alternatives, such as soy, almond, rice, or coconut milk fall short both in flavor and in functionality; moreover, a large part of the industrial and cultural significance of dairy milk stems from its usefulness in derivative products, such as cheese, yogurt, cream, or butter. Non-dairy plant-based milks, while addressing environmental and health concerns (and while providing adequate flavor for a small segment of the population), almost universally fail to form such derivative products when subjected to the same processes used for dairy milk.

Moreover, recent report from IATP noted, that as of 2017, the 13 top dairy companies' emissions grew 11% compared with 2015, corresponding to a 32.3 million metric ton increase in greenhouse gases equivalent to the emissions that would be released by adding an extra 6.9 million cars to the road for a year.

Therefore, the need exists for methods, systems and compositions for use in the in-vitro production of milk, milk proteins (e.g., casein, whey) and milk products.

SUMMARY OF THE INVENTION

Disclosed, in various implementations, are systems, compositions and methods for in-vitro production of milk using an array of mammary organoids. In other implementations, provided herein are methods for bio-printing of biostructures having a predetermined three dimensional structure with cells incorporated therein in a non-random two- and three dimensional pattern. In an exemplary implementation, provided herein is a system for in-vitro production of milk comprising: an array of vessels, each vessel comprising a plurality of mammary organoids (MO); a nutrient supply reservoir operable to feed each vessel; a milk collection module, in communication with each vessel, operable to collect milk produced by the MO; and a central processing module (CPM) in communication with the vessels' array, the nutrient supply reservoir, and the milk collection module, the CPM being in further communication with at least one processor and a memory storage device, storing thereon a processor readable medium with a set of executable instructions, configured when executed to cause the at least on processor to control the operation of each of the vessels' array, the nutrient supply reservoir, and the milk collection module, wherein the milk collected does not comprise nutrients supplied.

In another exemplary implementation, provided herein is a method of producing milk in-vivo, implementable in a system comprising an array of vessels, each vessel comprising a plurality of mammary organoids (MO); a nutrient supply reservoir operable to feed each vessel; a milk collection module, in communication with each vessel, operable to collect milk produced by the MO; and a central processing module (CPM) in communication with the vessels' array, the nutrient supply reservoir, and the milk collection module, the CPM being in further communication with at least one processor and a memory storage device, storing thereon a processor readable medium with a set of executable instructions, configured when executed to cause the at least on processor to control the operation of each of the vessels' array, the nutrient supply reservoir, and the milk collection module, wherein the milk collected does not comprise nutrients supplied, the method comprising: using the nutrient supply reservoir, contacting the MOs with the nutrients; and using the milk collection module, collecting milk secreted by the MOs.

In yet another exemplary implementation, each vessel included in the systems and the methods implemented thereby further comprise a tertiary-branched, resilient scaffolding of hollow tubes in liquid communication with the nutrient supply reservoir and wherein the plurality of MOs are operably coupled to the resilient tertiary-branched scaffolding.

In another exemplary implementation, the nutrient supply reservoir included in the systems and the methods implemented thereby further comprises: a first sub-reservoir with a composition comprising effective concentration of estrogen and progesterone; a second sub-reservoir with a composition comprising lactation medium; a third sub-reservoir with a composition comprising growth factor medium; and a fourth sub-reservoir with a composition comprising contraction medium.

BRIEF DESCRIPTION OF THE SEVERAL VIEWS OF THE DRAWING(S)

Figure 2:
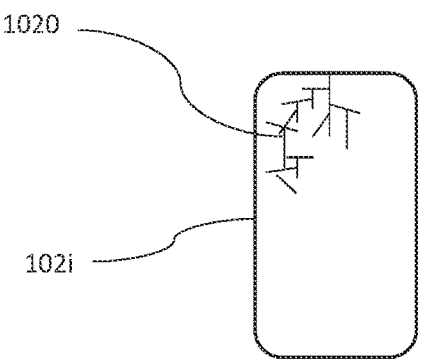

For a better understanding of the systems, compositions and methods for in-vitro production of milk using an array of mammary organoids, with regard to the exemplary implementations thereof, reference is made to the accompanying examples and figures, in which:

FIG. 1 is a schematic of an exemplary implementation of the system used to implement the methods disclosed; and FIG. 2 is a schematic of an exemplary implementation of the tertiary-branched resilient scaffolding tubes.

DESCRIPTION OF SPECIFIC EMBODIMENTS OF THE INVENTION

Provided herein are implementations of systems, compositions and methods for in-vitro production of milk using an array of mammary organoids. The exemplary implementations of the systems and compositions for implementing the methods disclosed, are adapted to provide a continuous production of milk.

Mammary epithelial cells secrete milk constituents by several routes. Milk lipid is enveloped by a milk fat globule membrane (MFGM) derived from the apical cell surface, and contains some of its constituent proteins. Soluble milk proteins are secreted by exocytosis. Three dimensional mammary epithelial cells culture (organoids) can be prepared from tissue of non-lactating, late-pregnant cows by, for example collagenase digestion and typical commercial isolation techniques (e.g., centrifugation, HPLC and the like). Cells can be cultured directly on scaffolding, embedded in a reconstituted basement membrane and further cultured in serum-free medium containing lactogenic hormones (e.g., estrogen, progesterone and prolactin). The cells form multicellular structures (mammary organoids) covered in matrix ("MOs"), and so long as they are contacted with prolactin, nutrients and growth factors in a controlled manner, do secrete milk for a period of between 10-21 days.

Accordingly and in an exemplary implementation, and as illustrated schematically in FIG. 1, provided herein is system 10 for in-vitro production of milk comprising: an array 101 of vessels 102$i$, each $i^{th}$ vessel comprising a plurality of mammary organoids (MO); nutrient supply reservoir 103 operable to feed each $i^{th}$ vessel; milk collection module 104, in communication with each $i^{th}$ vessel, operable to collect milk produced by the MO; and central processing module (CPM) 105 in communication with vessels' 102$i$ array 101, nutrient supply reservoir 103, and milk collection module 104, CPM 105 being in further communication with at least one processor and a memory storage device, storing thereon a processor readable medium with a set of executable instructions, configured when executed to cause the at least on processor to control the operation of each of: vessels' 102$i$ array 101, nutrient supply reservoir 103, and milk collection module 104, wherein the milk collected does not comprise nutrients supplied.

In the context of the disclosure, the term mammary organoid means three-dimensional mammary epithelial cells inside collagen, or other proteinaceous matrices, combining the advantages of easy manipulation of 2D cellular systems with providing complex cell-cell and cell-ECM interactions. The organoids are isolated in an exemplary implementation from bovine, goat, sheep, or other mammalian udder using typical processes and coupled to the scaffolding such that each $i^{th}$ vessel has between about 250 and 2500 MOs per vessel.

In the systems and methods disclosed, each vessel is selectably (in other words, without affecting the function or structure of any other component in the system) removable from the vessels' array. In other words, the vessel array is a modular bio-reactor where individual vessels (see e.g., 102$i$, FIG. 1). The selectable removal is in an exemplary implementation beneficial to maintain optimal milk production per vessel, allowing for replacement of vessels upon determination of malfunction, such as for example, contamination, cell division above a given threshold (e.g., 15-24 divisions), MOs that have prematurely undergone involution and the like. Furthermore, each vessel used in the systems disclosed herein, comprises in certain implementations, a tertiary-branched, resilient scaffolding of hollow tubes in liquid communication with the nutrient supply reservoir and wherein the plurality of MOs are operably coupled to the tertiary-branched scaffolding (see e.g., FIG. 2).

In the context of the current disclosure, the term "scaffold", or "scaffolding" refers in an exemplary implementation, to an engineered platform having a predetermined three dimensional structure, which mimic the 3D environment of the mammary ductal system, provide short term mechanical support of the MOs, and provide an increased surface area for cells adhesion, proliferation, migration, and differentiation, eventually leading to accelerated tissue formation of the functional MOs. Additionally or alternatively, "scaffolding" refers to a fabricated systems of conduits, sized adapted configured, to maintain fluid communication within the growing MOs to nutrients, buffer fluids, functionalizing fluids and other similar functional liquids. As indicated, the scaffold can also be a composite scaffold. A "composite scaffold" refers to a scaffold platform which is engineered in order to support colonization and/or proliferation of two or more tissue types which together comprise a "heterogeneous tissue". In certain implementations, the MOs are adhered to the resilient hollow tubes such that luminal cells are initially adhered to the tertiary-branched resilient scaffold tubes and basally situated myoepithelial cells.

Likewise, the term "tertiary branched" refers to ducts that brunch from branched ducts, all from a single trunk in each vessel, such that each vessel is in liquid communication with a manifold feeding each vessel in the array, connected to the nutrient reservoir. The duct diameter of the main trunk can be between about 0.5 mm and about 3 mm, and each primary branch between about 0.5 mm and about 2 mm, a secondary branch can be between about about 0.5 mm and about 1.5 mm, and a tertiary branch can be between about 0.5 mm and about 1 mm. In certain implementation, a pump, included with the nutrient reservoir is sized and configured to deliver the nutrient composition to all branches, taking into consideration the pressure drop associated with the degree of branching.

In certain exemplary implementations, the scaffolding may be a resilient ducts and can be, for example, poly (ethylenenaphthalate) (PEN), polyimide (e.g. KAPTONE® by DuPont), silicon ducts etc.

The milk collection module used in the systems disclosed can further include a vacuum source, such as a vacuum pump that can be a positive displacement pump, centrifugal pump, or a Venturi tube. Likewise, the pump delivering the nutrients' composition to the vessels' array, can be a positive displacement pump, a diaphragm pump, or a triplex pump. The milk collection module is in liquid communication with the vessels' array such that any milk secreted by the MOs, will not be in contact with the nutrient stream, thus obviating the need to separate the milk from the nutrients.

In certain embodiments, each $i^{th}$ vessel is embedded in gel, such as, for example, a composition comprising between about 50% (v/v) and about 70% (v/v) laminin, between about 20% (v/v) and about 40% (v/v) collagen, and between about 5% (v/v) and 10% (v/v) of nidogen.

In an exemplary implementation, the nutrient supply reservoir used in the systems disclosed, comprises: first sub-reservoir 1031 with a composition comprising effective concentration of estrogen and progesterone; second sub-reservoir 1032 with a composition comprising lactation medium; third sub-reservoir 1033 with a composition comprising growth factor medium; and fourth sub-reservoir 1034 with a composition comprising contraction medium (e.g., oxytocin).

Upon seeding of the scaffolding with the MO, estrogen and progesterone are instrumental in inducing growth and morphogenesis of epithelium via induction of paracrine signaling between mammary stroma and epithelium comprising the seeded MOs. Furthermore, lactation medium composition can comprise prolactin (e.g., retrieved from the pituitary gland of the same mammal that was used to harvest the MOs, or a recombinant prolactin, configured to increase lactation over that associated with the prolactin isolated from the reference mammal), configured to acts directly on prolactin receptor on luminal cells included in the MOs and is operable triggers alveoli maturation and lactogenic differentiation. Likewise, growth factor medium, can be for example basal organoid medium (BOM) supplemented with growth factors, such as, for example, FGF2, FGF7, FGF10, EGF, TGFα, WNT3A, R-spondin, or growth factor composition comprising one or more of the foregoing. Accordingly and in certain exemplary implementations, the set of executable instructions, is configured when executed to cause the at least on processor to, based on a predetermined sequence: controllably contact the vessel array with at least one of: the composition of the first, second, third and fourth sub reservoirs. In an exemplary implementation, the MOs are pretreated with FGF2, configured to accelerate lactogenic differentiation.

In addition, the vessels array, is enclosed in certain exemplary implementations, in a housing, operable to maintain the vessels in a controlled atmosphere, meaning, an atmosphere having gaseous composition that is different than air, for example enriched in CO2, and reduced in Nitrogen. Other sensors can be incorporated into the housing, for example, thermometers, hygrometers and the like. Furthermore, determining optimal milk production and determination of the selective replacement of a particular vessel, can be done for example, by monitoring the production of Csn2, and WaP proteins.

In the context of the disclosure, the term "operable" means the system and/or the device (e.g., the nutrient dispensing pump) and/or the program, or a certain element, component or step is/are fully functional sized, adapted and calibrated, comprising elements for, having the proper internal dimension to accommodate, and meets applicable operability requirements to perform a recited function when activated, coupled or implemented, regardless of being powered or not, coupled, implemented, effected, actuated, realized or when an executable program is executed by at least one processor associated with the system, method, and/or the device.

In some exemplary implementations, the systems disclosed are used to implement the methods provided. Accordingly and in yet another exemplary implementation, provided herein is a method of producing milk in-vivo, implementable in a system comprising an array of vessels, each vessel comprising a plurality of mammary organoids (MO); a nutrient supply reservoir operable to feed each vessel; a milk collection module, in communication with each vessel, operable to collect milk produced by the MO; and a central processing module (CPM) in communication with the vessels' array, the nutrient supply reservoir, and the milk collection module, the CPM being in further communication with at least one processor and a memory storage device, storing thereon a processor readable medium with a set of executable instructions, configured when executed to cause the at least on processor to control the operation of each of the vessels' array, the nutrient supply reservoir, and the milk collection module, wherein the milk collected does not comprise nutrients supplied, the method comprising: using the nutrient supply reservoir, contacting the MOs with the nutrients; and using the milk collection module, collecting milk secreted by the MOs, the method further comprising controllably contacting the vessel array with at least one of: the composition of the first, second, third and fourth sub reservoirs. For example, the following differentiation, the system can be configured to deliver a predetermined combination of growth factor(s) and other medium (e.g., lactation medium) together, to enhance production of other milk components, such as fat globules, Csn2, and WaP proteins.

In relation to systems and methods disclosed, the term "operable" also means the system and/or the circuit is fully functional and calibrated, comprises logic for, and meets applicable operability requirements to perform a recited function when executed by at least one processor The term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

All ranges disclosed herein are inclusive of the endpoints, and the endpoints are independently combinable with each other. "Combination" is inclusive of blends, mixtures, alloys, reaction products, and the like. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the image(s) includes one or more images). Reference throughout the specification to "one implementation", "another implementation", "an exemplary implementation,", and so forth, when present, means that a particular element (e.g., feature, structure, and/or characteristic) described in connection with the implementation is included in at least one implementation described herein, and may or may not be present in other implementations. In addition, it is to be understood that the described elements may be combined in any suitable manner in the various implementations.

All ranges disclosed herein are inclusive of the endpoints, and the endpoints are independently combinable with each other. Furthermore, the terms "first," "second," and the like, herein do not denote any order, quantity, or importance, but rather are used to denote one element from another.

Likewise, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. For example, "about" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

Although the foregoing disclosure for systems, compositions and methods for in-vitro production of milk using an array of mammary organoids seeded on tertiary-branched, resilient duct scaffolding has been described in terms of some implementations, other implementations will be apparent to those of ordinary skill in the art from the disclosure herein. Moreover, the described implementations have been presented by way of example only, and are not intended to limit the scope of the inventions. Indeed, the novel methods, programs, libraries and systems described herein may be embodied in a variety of other forms without departing from the spirit thereof. Accordingly, other combinations, omissions, substitutions and modifications will be apparent to the skilled artisan in view of the disclosure herein.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for in-vitro production of milk comprising:
   a. an array of vessels, each vessel comprising multicellular structures of mammary cells operably coupled to a tertiary-branched scaffold of hollow tubes;
   b. a nutrient supply reservoir operable to feed each vessel;
   c. a milk collection module, in communication with each vessel such that milk produced by said mammary cells is not in contact with nutrient stream from said nutrient supply reservoir;
   d. a central processing module (CPM) in communication with said vessels' array, said nutrient supply reservoir, and said milk collection module, said CPM being in further communication with at least one processor and a memory storage device, storing thereon a processor readable medium with a set of executable instructions, configured when executed to cause said at least on processor to control operation of each of the vessels' array, said nutrient supply reservoir, and said milk collection module;
   e. a housing operable to maintain controlled atmosphere over said vessel array.

2. The system of claim 1, wherein each vessel is selectably removable from said vessels' array.

3. The system of claim 1, wherein said milk collection module further comprises a vacuum source.

4. The system of claim 1, wherein said tertiary-branched scaffold of hollow tubes, and said mammary cells are embedded in a gel.

5. The system of claim 4, wherein said gel is comprised of a composition comprising between about 50% (v/v) and about 70% (v/v) laminin, between about 20% (v/v) and about 40% (v/v) collagen, and between about 5% (v/v) and 10% (v/v) of nidogen.

6. The system of claim 1, wherein said mammary cells comprise post-parturition mammary epithelium cells.

7. The system of claim 1, wherein said nutrient supply reservoir comprises:
   a first sub-reservoir with a composition comprising effective concentration of estrogen and progesterone;
   a second sub-reservoir with a composition comprising lactation medium;
   a third sub-reservoir with a composition comprising growth factor medium; and
   a fourth sub-reservoir with a composition comprising contraction medium.

8. The system of claim 7, wherein said set of executable instructions, is configured when executed to cause said at least on processor to, based on a predetermined sequence: controllably contact said vessel array with at least one of: the composition of the first, second, third and fourth sub reservoirs.

9. A method of producing milk, implementable in the system of claim 1, the method comprising:
   using said nutrient supply reservoir, contacting the mammary cells with nutrients; and
   using said milk collection module, collecting milk secreted by said mammary cells.

10. The method of claim 9, wherein said milk collection module further comprises a vacuum source.

11. The method of claim 9, wherein said tertiary-branched scaffold of hollow tubes, and said mammary cells coupled thereto are embedded in a gel.

12. The method of claim 9, wherein said mammary cells comprise post-parturition mammary epithelium cells.

13. The method of claim 9, wherein said nutrient supply reservoir comprises:
   a first sub-reservoir with a composition comprising effective concentration of estrogen and progesterone;
   a second sub-reservoir with a composition comprising lactation medium;
   a third sub-reservoir with a composition comprising growth factor medium; and
   a fourth sub-reservoir with a composition comprising contraction medium.

14. The method of claim 13, further comprises a housing operable to maintain controlled atmosphere over the vessel array.

15. The method of claim 13, further comprising controllably contacting the vessel array with at least one of: the composition of the first, second, third and fourth sub reservoirs.

16. The system of claim 1, wherein said multicellular structures comprise luminal cells and myoepithelial cells and wherein said luminal cells are adhered to the tertiary-branched scaffold tubes and basally situated myoepithelial cells.

17. The method of claim 9, wherein said multicellular structures comprise luminal cells and myoepithelial cells and wherein said luminal cells are adhered to the tertiary-branched scaffold tubes and basally situated myoepithelial cells.

* * * * *